United States Patent [19]

Kocal et al.

[11] Patent Number: 4,677,245
[45] Date of Patent: Jun. 30, 1987

[54] NOVEL MOTOR FUEL ALKYLATION PROCESS

[75] Inventors: Joseph A. Kocal, Gurnee; Tamotsu Imai, Mount Prospect, both of Ill.

[73] Assignee: UOP Inc., Des Plaines, Ill.

[21] Appl. No.: 927,462

[22] Filed: Nov. 6, 1986

Related U.S. Application Data

[63] Continuation of Ser. No. 791,289, Oct. 25, 1985, Pat. No. 4,634,801, which is a continuation of Ser. No. 764,707, Aug. 12, 1985, Pat. No. 4,636,488.

[51] Int. Cl.$^4$ ................................................ C07C 2/58
[52] U.S. Cl. ...................................... 585/724; 585/732
[58] Field of Search ................................. 585/724, 732

[56] References Cited

U.S. PATENT DOCUMENTS 3,778,489 12/1973 Parker et al. ......................... 585/724

Primary Examiner—Curtis R. Davis
Attorney, Agent, or Firm—Thomas K. McBride; John F. Spears, Jr.

[57] ABSTRACT

A novel hydrocarbon alkylation process is disclosed wherein the feed hydrocarbons are dried to maintain the water content of the alkylation catalyst at less than 2.0 wt. %, where said alkylation catalyst is comprised of a mineral acid and an ether component selected from the group consisting of tert-butyl ether, methylphenyl ether, tert amylmethyl ether (TAME), or methyl tert-butyl ether (MTBE). This process also incorporates a method of regenerating at least a portion of the alkylation catalyst to prevent build-up of more than 15 wt. % of polymer products therein.

7 Claims, 1 Drawing Figure

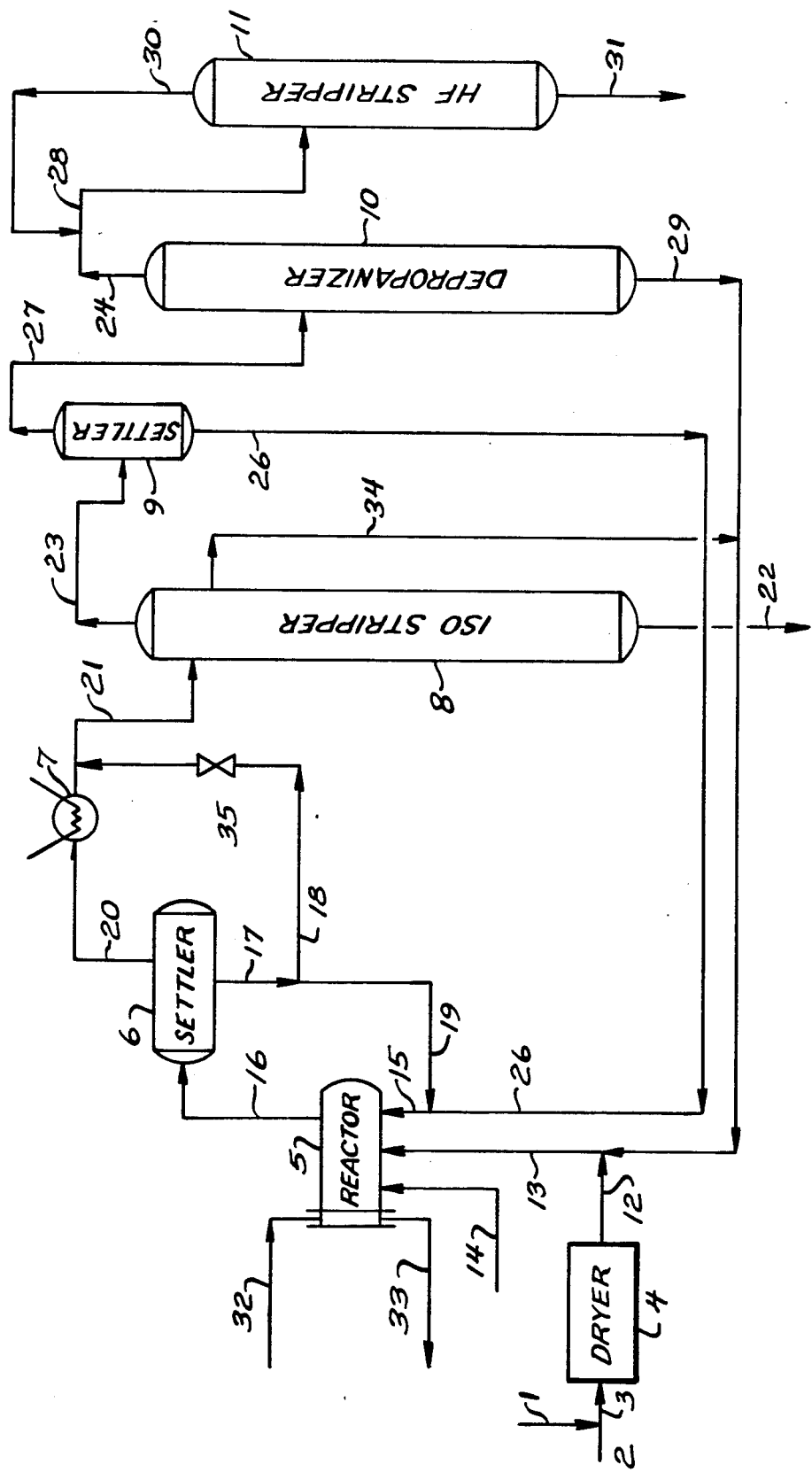

NOVEL MOTOR FUEL ALKYLATION PROCESS

CROSS-REFERENCE TO RELATED APPLICATIONS

This application is a continuation of prior copending application Ser. No. 791,289 filed Oct. 25, 1985, now U.S. Pat. No. 4,634,801, which is a continuation of prior copending application Ser. No. 764,707, filed Aug. 12, 1985, now U.S. Pat. No. 4,636,488, the contents of which are incorporated by reference thereto.

BACKGROUND OF THE INVENTION

This invention relates to a process for the alkylation of an isoparaffin with an olefin-acting agent. Additionally, the invention relates to a process in which a novel catalyst is used to produce an alkylate having improved antiknock properties. Accordingly, the invention has particular utility in the production of high octane alkylate for use as a motor fuel blending component.

Alkylation of isoparaffinic hydrocarbons, such as isobutane and isopentane, with olefinic hydrocarbons such as propylene, butylene and amylenes or with other olefin-acting agents such as $C_3$-$C_5$ alkyl halides, etc., using mineral acids such as hydrogen fluoride is well known as a commercially important method for producing gasoline boiling range hydrocarbons. The $C_5$-$C_{10}$ hydrocarbons typically produced in isoparaffin-olefin alkylation operations are termed "alkylate". Alkylate is particularly useful as a motor fuel blending stock. It possesses motor and research octane ratings high enough that it may be employed to improve overall octane ratings of available gasoline pools to provide motor fuels which comply with the requirements of modern automobile motors. High octane alkylate blending components are particularly important in producing motor fuels of sufficiently high octane when it is desired to avoid use of alkyl lead antiknock compounds is gasoline. A continuing goal in the art is to provide an economically attractive acid catalyzed alkylation process which provides an alkylate product having motor and research octane ratings which are higher than are attainable in conventional alkylation processes. This goal takes on special significance with the phaseout of alkyl lead antiknock compounds as blending agents for gasoline as mandated by government regulation.

In commercial isoparaffin-olefin alkylation operations using acid catalysts, generally, isobutane is the isoparaffin used and propylene, butylene and amylenes or a mixture of these olefins, are used as the olefin-acting agent. Typically the acid catalyst will comprise hydrogen fluoride. In conventional operations, the isoparaffin, olefin-acting agent and hydrogen fluoride catalyst are first contacted and thoroughly admixed in an alkylation reactor, forming a reaction mixture, or emulsion. After a relatively short time, the alkylation reaction is substantially complete and the reaction mixture is withdrawn from the alkylation reactor and is allowed to settle by gravity into immiscible hydrocarbon and catalyst phases in a settling vessel. The hydrogen fluoride catalyst phase thus separated is returned to the alkylation reactor for further catalytic use. The hydrocarbon phase separated in the settling operation is further processed, e.g., by fractionation, to recover an alkylate product and to separate unconsumed isoparaffin for recycle to the alkylation reactor. The recovered alkylate product may then be added to the motor fuel octane pool as a blending component. It is, therefore, desirable that the alkylate product has as high a research octane number as possible.

OBJECTS AND EMBODIMENTS

It is, therefore, an object of the present invention to provide an improved process for the alkylation of an isoparaffin with an olefin-acting agent. An alternative object is to employ the improved process to produce an alkylate having good antiknock properties.

Accordingly, in one embodiment the present invention is a process for the alkylation of an isoparaffin with an olefin-acting agent in the presence of an alkylation catalyst comprising the steps of (a) drying the olefin-acting agent and at least a portion of the isoparaffin in a drying means to produce a dried alkylation feedstock wherein said drying is performed such that the water content of the alkylation catalyst is maintained at less than 2.0 wt.% based on the total weight of the catalyst; (b) contacting the dried alkylation feedstock and recycled paraffin with the alkylation catalyst which catalyst comprises an anhydrous mixture of from about 0.1 to about 15 wt.% of an ether component selected from the group consisting of tert-butyl ether, methylphenyl ether, tert-amylmethyl ether (TAME), or methyl tert-butyl ether (MTBE) and at least 80 wt.% mineral acid in a reaction zone at alkylation conditions and producing a reaction product effluent containing (i) normally liquid alkylate, (ii) unreacted isoparaffin, (iii) alkylation catalyst, and (iv) polymer products; (c) separating the reaction product effluent in a separation zone into (i) a liquid hydrocarbon phase and, (ii) a liquid alkylation catalyst phase containing polymer products; (d) regenerating at least a portion of the liquid alkylation catalyst phase at a rate sufficient to provide a polymer products concentration in the liquid alkylation catalyst phase of less than 15 wt.% based on the total weight of the liquid alkylation catalyst phase.

These as well as other objects and embodiments will become apparent upon review of the following more detailed description of the prior art and the invention.

INFORMATION DISCLOSURE

The art has recognized a number of alkylation process schemes employing a variety of acid alkylation catalyst containing various modifiers. For example, U.S. Pat. No. 3,761,540 discloses that an isoparaffin may be alkylated with an olefin using hydrogen fluoride catalyst and a small proportion of $BF_3$. The $BF_3$ is disclosed as modifying the alkylation reaction in such a fashion as to minimize production of ethyl fluoride. The reference discloses that when the isoparaffin to olefin ratio in the reaction zone is less than about 4:1, a high octane value alkylate may be made by modifying the HF catalyst with $BF_3$ while minimizing alkyl fluoride formation.

U.S. Pat. No. 3,531,546 discloses the alkylation of organic compounds in the presence of a novel catalyst comprising a hydrogen fluoride-carbon dioxide complex. It is disclosed that by using the hydrogen fluoride-carbon dioxide complex, a motor fuel alkylate having increased research octane number is thereby produced. The increased octane number results from improved isomer distribution in the alkylate.

Of particular interest is U.S. Pat. No. 3,778,489. This reference discloses an alkylation process for alkylating alkanes with an alkene utilizing various strong acids including hydrofluoric acid in the presence of a catalyst promoter. At column 3, line 61 of the reference, it is disclosed that the preferred catalyst promoters contain either a hydroxy group such as alcohols or a hydroxy group precursor such as ethers *which cleave to form alcohols* under the acidic conditions of the subject invention. The most preferred compounds are disclosed to be the lower molecular weight alcohols such as ethyl alcohol, the lower molecular weight ethers such as diethyl ether and water. Accordingly, this reference discloses that ether compounds may be employed in the alkylation of alkanes and alkenes under conditions which promote the cleavage of the ethers to form alcohol. These ethers, therefore, do not act as catalyst in that they are not inert but rather cleave to form different compounds and are thereby consumed in the alkylation reaction. By way of distinction, the present invention employs ether compounds as actual catalyst components, the conditions within the alkylation process being such to preserve the ether and inhibit any cleavage thereof to an alcohol.

In summary then the art has disclosed the use of catalyst promoters and in particular has disclosed the use of ether as a precursor of an alcoholic promoter. However, the art has not disclosed a catalyst comprising a strong acid such as hydrofluoric acid and an ether compound in which catalyst, the ether is maintained as an ether as opposed to being cleaved to an alcohol. Rather, in the instant invention the ether acts as a true catalyst component being substantially unconsumed in the alkylation process. By means of the novel process of the instant invention, a substantial increase in the product alkylate quality, specifically as increased octane, is realized with only a marginal increase in operating costs.

DETAILED DESCRIPTION OF THE INVENTION

As hereinabove set forth, the present invention is directed toward an improvement in a process for alkylating an isoparaffin with an olefin-acting agent. Although particularly applicable to the alkylation of isobutane with olefin-acting agents comprising $C_3$–$C_5$ olefins, the process is also adaptable for utilization with other isoparaffinic and olefinic feedstocks for the purposes of producing motor fuel or aviation alkylates.

Typical of the isoparaffins which may be utilized in the invention are isobutane, isopentane and similar isoparaffins. The preferred isoparaffins are isobutane and isopentane, particularly, isobutane. A mixture of two or more isoparaffins may also be employed, if desired. Conventional isobutane alkylation feedstocks are suitable for use in the present process. Such conventional isobutane feedstocks may contain some nonreactive hydrocarbons such as normal paraffins. For example, a conventional commercial isobutane alkylation feedstock generally contains about 95 wt.% isobutane, 4 wt.% normal butane and 1 wt.% propane.

Olefin-acting agents which are suitable for use in the process of the present invention include $C_3$–$C_6$ monoolefins, alkyl halides, or mixtures thereof. $C_3$–$C_5$ olefins are preferred. The process of the present invention may be applied to the alkylation of mixtures of two or more olefin-acting agents with the same benefits and improvements as would be obtained in using a single olefin-acting agent. For example, many conventional olefin feedstocks utilized in commercial alkylation operation contain mixtures of propylene and butylenes, or propylene, butylenes and amylenes. Application of the present process to such olefin mixtures results in improvements in quality of the products obtained which are equal to the improvement obtained using a single olefin. Similarly, a mixture of $C_3$–$C_5$ alkyl halides and olefins in any proportion is also suitable in many cases, for example, when the halide is fluoride. The particularly preferred $C_3$–$C_5$ olefin feedstocks are conventionally derived from petroleum refining processes such as catalytic cracking and may contain substantial amounts of paraffins, lighter and heavier olefins, etc. Olefin feedstocks derived from such conventional sources are suitable for use in providing the olefin-acting compound used in the present process.

As heretofore indicated, it is essential that the water content of the alkylation catalyst be maintained at less than 2.0 and preferably less than 1.5 wt.% based on the total weight of the catalyst. Control of the water content of alkylation catalyst is important for two reasons. First, excessive amounts of water reduce the alkylation activity of the catalyst and introduces severe corrosion problems into the system. The second reason is of critical importance in this process, that being to prevent degradation of the ether component of the catalyst. Degradation occurs as a result of hydrolysis of the ether, thereby causing the formation of the corresponding alcohol. Since the hydrolysis reaction can be effected with low levels of water, it is necessary in the instant process to maintain the water content of the catalyst to less than 2.0 wt.%, based on the total weight of the catalyst. This is accomplished by drying the olefin-acting agent and at least a portion of the isoparaffin in a drying means, thereby producing a dried alkylation feedstock. Any drying means known to the art is suitable, such as conventional solid adsorbent having a high selectivity for water, sodium or calcium crystalline aluminosilicates, silica gel, activated alumina, molecular sieves, anhydrous calcium sulfate, high surface area sodium, and the like absorbents. Similarly, the water content of the feedstock may be adjusted by suitable stripping operations in a fractionation column or like device. And in some cases, a combination of adsorbent drying and distillation drying may be used advantageously to effect removal of water from the feedstock. The preferred drying means is molecular sieves operating at a temperature ranging from about 40° F. (5° C.) to 200° F. (93° C.) and a pressure ranging from about 100 psig to 400 psig.

Another essential feature of the instant invention is the particular alkylation catalyst specified. The catalyst used in the process of the present invention comprises a mixture of a mineral acid and an ether component. Further, it is particularly desirable that the water content of the alkylation acid should comprise no more than about 2.0 wt.% based on the total weight of the catalyst phase.

Mineral acids which may be employed in the present invention comprise any mineral acid commonly used in alkylation processes. Such acids include sulfuric acid, halosulfuric acids such as fluorosulfuric acid or halogen acids such as hydrofluoric acid, etc. It is to be further understood that the term "mineral acid" is intended to encompass solid acid sources such as acidic resins or zeolites which are suitable for catalyzing the alkylation of an isoparaffin with an olefin-acting agent. Especially preferred is the use of hydrofluoric acid.

Hydrofluoric acid is preferred because it is one of the most stable mineral acids. It can be subjected to high temperatures and pressures and to the action of other catalytic agents without being broken down. Many of its organic compounds decompose either by heat alone or in the presence of catalyst to regenerate hydrofluoric acid. This results in low catalyst consumption in the process. An important advantage of using hydrofluoric acid is that by virtue of its chemical stability and low freezing point, it may be employed over a wide range of operating conditions. Conditions may be employed which are most satisfactory thermodynamically or economically, without limitations due to catalyst properties. For example, in the alkylation reaction, ambient or slightly superambient temperatures may be used with hydrofluoric acid. Hence, it is unnecessary to utilize refrigeration as might be the case when certain other mineral acids are utilized as the alkylation catalysts. The vapor pressure of hydrofluoric acid makes it unnecessary to resort to extreme pressures to maintain the catalyst in liquid phase. Its freezing point permits its use at temperatures much lower than is possible with most catalysts which either freeze or become highly viscous at low temperatures. Although in the alkylation of isobutane with olefins to produce aviation blending fuel, the usual operating conditions are of the order of about 30° C., there are catalytic reactions which are favored by low temperatures. Since hydrofluoric acid catalyzes such reactions, it is a distinct advantage because of its physical properties. Conversely, since hydrofluoric acid is thermally stable it can be employed at much higher temperatures than other alkylation catalysts. This is a unique property of hydrofluoric acid.

As heretofore indicated, the catalyst of the present invention comprises from about 70 to about 99.5 wt.% mineral acid based on the weight of the acid catalyst. It is especially preferred that the invention comprise at least 80 wt.% mineral acid. This is especially true when the acid comprises hydrofluoric acid. A particularly preferred catalyst composition comprises about 90 wt.% hydrofluoric acid based on the weight of the acid phase.

The second component of the alkylation catalyst is an ether component. As heretofore indicated, the art has been cognizant of utilizing ether as an additive for alkylation processes; however, in the prior art the ether was taught to be an alcohol precursor. Accordingly, the prior art is directed towards an alkylation process wherein an alcohol or alcohol precursors comprise a catalyst modifier. In contradistinction, the present invention is directed toward a catalyst wherein the ether component is a true catalyst component in that the ether is not consumed in the reaction.

Any suitable ether may be utilized as the ether component provided, however, that such an ether does not undergo hydrolysis. For example, the ether component may comprise lower molecular weight ether such as dimethyl ether, diethyl ether, dipropyl ether, etc. It is preferred, however, that the ether component comprises an ether that will be liquid at the conditions employed within the alkylation reaction zone. It is particularly preferred that the ether component be selected from the group consisting of tert-butyl ether, methylphenyl ether, tert-amylmethylether (TAME), or methyl tert-butyl ether (MTBE). Of course, it should be understood that the ether component may comprise a single ether species such as methyl tert-butyl ether, or the ether component may comprise a mixture of two or more ethers. It is preferred that the ether component of the invention comprises between 0.1 and 15 wt.%, based on total catalyst weight. Especially preferred is an ether component concentration of from about 2 to 10 wt.%.

Another essential feature of the instant invention is to regenerate at least a portion of the liquid alkylation catalyst phase at a rate sufficient to provide a polymer products concentration in the liquid alkylation catalyst phase of less than 15 wt.% based on the total weight of the catalyst. Preferably, this concentration should be maintained in the range from about 2 to about 10 wt.% based on the total weight of the catalyst. These polymer products, sometimes referred to as either acid-soluble oils or organic diluent are typically formed during the alkylation reaction and appear in the alkylation catalyst phase removed from the lower portion of the settling means. Characterization of these polymer products is difficult because their formation is directly related to varying feedstock compositions and varying alkylation reactor process variables. Minimizing the amount of these polymer products is important for efficient utilization of the isoparaffin and olefin-acting agent. Excessive polymer product in the alkylation catalyst phase will promote further polymerization which eventually results in formation of undesirable tar compounds.

Removal of at least a portion of the liquid alkylation to a regeneration means will prevent polymer product built-up. Any regeneration means is suitable, including external fractionation, wherein a stream of alkylation catalyst containing polymer products is passed to a fractionation column, the acid and ether component is removed overhead to be returned to the reaction zone and the polymer products and any tar material present is removed as a bottoms waste stream. A preferred means of regenerating liquid alkylation catalyst involves an internal regeneration procedure as is set forth in U.S. Pat. No. 4,195,191, which is incorporated herein by reference.

This preferred regeneration procedure involves removing a portion of the settled catalyst phase from the reaction mixture settling means and introducing this portion directly into a fractionation column with the hydrocarbon phase from the settling means. The temperature of these streams, as they emanate from the settling means, is generally in the range of from about 68° F. (20° C.) to about 106° F. (41° C.). The temperature of only the hydrocarbon phase is increased to a level in the range of about 122° F. (50° C.) to about 201° F. (94° C.), to increase the solubility potential of HF therein, prior to the introduction thereof into the fractionation column. That portion of the alkylation catalyst phase, emanating from the settling zone, and not being recycled to the reaction zone, is not increased in temperature, but is commingled with the heated hydrocarbon phase and introduced therewith into the fractionation column. Within the fractionator, the hydrocarbon phase and the polymer products from the alkylation catalyst phase are separated from the alkylation catalyst and removed as a bottom product stream. The alkylation catalyst is removed as an overhead stream and typically undergoes further treatment before recycling to the reaction zone.

Alkylation conditions which may be employed in the process of the present invention include a temperature of from about 0° F. (−18° C.) to about 200° F. (93° C.), a pressure sufficient to maintain the reactants and the catalyst in the liquid phase, and a contact time between the hydrocarbons and the catalyst of about 0.1 minute to about 30 minutes.

In a particularly preferred embodiment, a reaction mixture of a catalyst comprising hydrogen fluoride and an ether component selected from the group consisting of tert-butyl ether, methylphenyl ether, tert amylmethyl ether (TAME), or methyl tert-butyl ether (MTBE), reactants and reaction products formed in the alkylation reactor is passed through a reaction soaker. Alternate reaction schemes to effect alkylation of the isoparaffin with the olefin-acting agent are within the scope of the instant invention, for example, the commonly used reaction riser method. In this method, the olefin-acting agent is mixed with the isoparaffin, either fresh or recycled, and fed into a riser reactor where it is mixed with the alkylation catalyst under pressure sufficient to maintain reactants in liquid phase. The riser reactor product effluent is then passed in a settling vessel where it is separated into a liquid hydrocarbon phase and a liquid alkylation catalyst phase containing polymer products. Removal of the heat of reaction occurs by passing the liquid alkylation catalyst through a heat exchange means prior to passing into the riser reactor. Multiple riser reactors with various alternatives for recycling of isoparaffin and alkylation catalyst is envisioned provided that the alkylation catalyst has a water content of less than 2.0 wt.% and a polymer products content of less than 15 wt.%, both based on the total weight of the liquid alkylation catalyst phase.

In the description of the preferred embodiments herein provided, it is intended that both the alkylation reactor and a reaction soaker, if one is utilized, are included within the scope of the term "alkylation reaction zone". Suitable reaction soakers are well known in the art. For example, the reaction soakers described in U.S. Pat. Nos. 3,560,587 and 3,607,970 may suitably be employed in the present process. Such reaction soakers are conventionally vessels equipped with perforated trays, baffle sections, or the like to maintain an alkylation reaction mixture in the form of a fairly homogeneous mixture, or emulsion, for a predetermined length of time. The alkylation reaction mixture of catalyst and hydrocarbons is maintained in the reaction soaker for a time which depends on the composition of the reaction mixture. Generally a reaction soaker residence time of about 1 minute to about 30 minutes is employed. The temperature and pressure maintained in the reaction soaker are substantially the same as the temperature and pressure maintained in the associated alkylation reactor.

Means for settling the reaction mixture effluent from the alkylation reaction zone in order to separate a settled hydrocarbon phase and an acid catalyst phase are well known in the alkylation art. Generally, the effluent alkylation reactor mixture recovered from an alkylation reactor or soaker comprises a mixture of unreacted isoparaffins, alkylation reaction products, acid catalyst, and catalyst-soluble organic materials, possibly with small amounts of light hydrocarbons, etc. When this alkylation reaction mixture is allowed to stand unstirred, i.e., settled, the alkylation reaction products, isoparaffins and light hydrocarbons form a lighter settled hydrocarbon phase. The acid catalyst phase comprising a mineral acid and ether component forms a separate phase. The settled hydrocarbon phase is then simply mechanically separated from the catalyst phase. The temperature and pressure maintained during such a settling operation are substantially the same as those described above in connection with the alkylation conditions employed in the reaction zone. The hydrocarbons and the catalyst are preferably in the liquid phase during the settling separation operation.

Some means for withdrawing heat from alkylation zone may be necessary for optimum operation of the process. A variety of means for accomplishing the heat withdrawal are well known. For example, the heat generated in the alkylation reaction may be withdrawn from the alkylation reactor by indirect heat exchange between cooling water and the reaction mixture in the reactor.

In further describing the instant invention, reference will be made to the accompanying drawing which is presented for the sole purpose of describing one type of alkylation process envisioned which includes the improvements of the present invention. In the drawing, the process is presented by means of simplified flow diagrams in which such details as pumps, instrumentation and controls, quench systems, heat-exchange and recovery circuits, valving, start-up lines, and similar hardware have been eliminated as being non-essential to an understanding of the techniques involved. The use of such miscellaneous appurtenances, to modify the process as illustrated, will be evident to those possessing skill in the art of petroleum refining technology.

Briefly, the drawing constitutes a simplified flow diagram of a typical present-day alkylation process which can be improved by incorporation therein of the present inventive concept. Illustrated are the principle vessels; feedstock dryer 4, reactor 5, catalyst-hydrocarbon settler 6, isostripper 8, isostripper settler 9, depropanizer 10, and HF stripper 11.

DESCRIPTION OF THE DRAWING

The drawing presents a schematic flow diagram representing a commercial unit designed for the alkylation of isobutane with a mixed olefin feed. The olefinic hydrocarbon stream enters the process via line 2 and make-up isobutane is introduced into the process via line 1. The olefinic hydrocarbon stream and make-up isobutane are combined by way of line 3 forming an alkylation feedstock which is then introduced into the alkylation feedstock dryer 4. The dried alkylation feedstock is removed from dryer 4 via line 12 and combined with an isobutane recycle stream line 29 prior to introduction via line 13 into alkylation reactor 5.

The reactor is designed to function as a heat exchanger having multiple feed injection points, which design is well known and not, therefore, illustrated herein. A portion of liquid alkylation catalyst, containing polymer products comprising approximately 89.5 wt.% hydrogen fluoride, 5.0 wt.% methyl tert-butyl ether, 0.5 wt.% $H_2O$ and 5.0 wt.% polymer products, is recycled from settler 6 by way of line 19, admixed with a second stream 26 of recycled alkylation catalyst, wherein substantially all of the polymer products have been removed from said second stream in isostripper 8, and introduced into reactor 5 by way of line 15. Make-up methyl tert-butyl ether may be introduced into reactor 5 via line 14 as needed to maintain the desired ether content of the liquid alkylation catalyst. In reactor 5, the isobutane/olefinic hydrocarbon mole ratio is about 10 and the HF acid/hydrocarbon volumetric ratio is about 1.5. Reactor 5 is maintained at a pressure of about 200 psig, with the liquid alkylation catalyst and reactant streams being introduced at a temperature of about 100° F. (38° C.).

Because the alkylation of an isoparaffin/olefin reactant mixture is highly exothermic, a cooling medium is required to temper the reaction. In the illustration, the heat of reaction is removed by introducing water by way of line 32 and removing by way of line 33. The total reaction product effluent is withdrawn from reactor 5 through line 16 at a temperature of about 100° F. (30° C.) and a pressure of about 200 psig.

The product effluent continues through line 16 into settler 6, wherein the effluent is settled into a liquid hydrocarbon phase and a liquid alkylation catalyst phase containing polymer products. The settled liquid alkylation catalyst phase containing polymer products is removed via line 17 with at least a portion being diverted through line 18 and a greater portion being recycled through line 19 as heretofore mentioned. The portion of alkylation catalyst in line 18 passes through containing valve 35 and is admixed, downstream of heat exchanger 7, with the liquid hydrocarbon phase in line 20 recovered from settler 6. The resultant admixture is introduced into isostripper 8 by way of line 21. Heat exchanger 7 is utilized to regulate the temperature of the material in line 21 entering isostripper 8. Although only one heat exchanger is illustrated, it is within the scope of the present invention to use as many heat exchangers as required to perform the desired degree of temperature regulation. Heat exchanger 7 can utilize, as the heating medium the hot effluent stream from the bottom of the isostripper, the hot effluent from the bottom of the depropanizer, or both. Other streams, such as isostripper side-cut vapor can also be used as the heating medium for exchanger 7.

Isostripper 8 operates at a top pressure of about 140 psig, a top temperature of about 130° F. (54° C.), a bottom temperature of about 350° F. (177° C.), and a bottom pressure of about 150 psig. A side-cut of primarily isobutane is recovered in line 34, mixed with depropanizer bottoms product in line 29 and is recycled via line 13 to the reaction vessel.

As previously set forth, the polymer products are removed in the isostripper and recovered through line 22 in admixture with the normally liquid alkylate product. Experience has proven that there is no product degradation stemming from the inclusion therein of these polymer products.

Overhead vapors from isostripper 8 consisting of a mixture of alkylation catalyst and hydrocarbons are withdrawn through line 23. Although not illustrated, a portion of this material in line 23 may be utilized as reflux to the top of isostripper 8. The material in line 23 is introduced into settler 9.

Settled alkylation catalyst is removed from settler 9 and recycled via line 26 to reactor 5. Hydrocarbons and alkylation catalyst are introduced via line 27 into depropanizer 10. A propane concentrate containing alkylation catalyst is recovered as an overhead stream in line 24, mixed with the material in line 30 recovered from the overhead of HF stripper 11, then introduced via line 28 into HF stripper 11. The bottoms stream from depropanizer 10, as previously set forth, is mixed with stream 34 and recycled to reactor 5. Depropanizer 10 functions with a bottom pressure of about 310 psig, a bottom temperature of about 220° F. (104° C.), a top temperature of about 140° F. (60° C.), and a top pressure of about 305 psig. Alkylation catalyst is withdrawn as an overhead stream in line 30 from HF stripper 11, and admixed with the isostripper overhead in line 23. Hydrocarbons are recovered via line 31. HF stripper 11 functions with a top temperature of about 140° F. (60° C.), a top pressure of about 340 psig, a bottom temperature of about 155° F. (68° C.), and a bottom pressure of about 343 psig.

The normally liquid alkylate product withdrawn via line 22, based on pilot plant experimentation utilizing similar process conditions, would have a Reid Vapor Pressure of 7 lbs., a clear octane rating of 96 RON, and a gravity of 71° API. The advantages of the instant invention are clearly apparent to those having skill in the art of petroleum refining technology.

In order to demonstrate the benefits and advantages of the present invention in contrast to the prior art alkylation processes, the following examples are offered. It is to be understood that the examples are intended to be illustrative and in no way restrictive on the otherwise broad embodiments of the present invention as set forth in the claims appended hereto.

EXAMPLE I

The alkylation process of the instant invention was evaluated in a pilot plant scale alkylation unit. This example shows the improved performance when using either a catalyst comprised of HF/tert-butyl ether or HF/methylphenyl ether. The pilot plant comprised a monel autoclave in which the isoparaffin and olefin-acting agent are contacted with the acid catalyst. After sufficient time, the hydrocarbon and acid phases were removed from the autoclave and passed to a settler in which the phases were allowed to separate. The acid phase was then removed from the settler and recycled back to the autoclave for contact with more hydrocarbon. The hydrocarbon phase comprising alkylate was removed from the settler and passed to neutralization facilities. Thereafter the hydrocarbon phase was collected for analysis.

In this example, four different runs were made in the pilot plant. Run A employed an alkylation catalyst comprising approximately 13 wt.% tert-butyl ether and 87 wt.% hydrogen fluoride. Run B employed an alkylation catalyst comprising approximately 12 wt.% methylphenyl ether and 88 wt.% hydrogen fluoride. Run C employed a catalyst comprising approximately 10 wt.% methyl tert-butyl ether and 90 wt.% hydrogen fluoride. The fourth run, Run D, was not the process of the instant invention. Run D employed a catalyst comprising only hydrogen fluoride as the catalytic component and was performed as a benchmark to compare the processes of the instant invention, i.e., Runs A, B, and C. In both tests, the conditions within the autoclave were a temperature of 68° F. (20° C.), a pressure of 130 psig, a hydrocarbon residence time of 25 minutes, a stirring rate of 1800 rpm, and a volume ratio of acid phase to hydrocarbon phase (excluding the ether component of the catalyst) in the autoclave of 1.5. The mole ratio of isobutane to $C_4$ olefins was 7.9. The $C_4$ olefin distribution was 48.2% 2-butene, 23.2% 1-butene, and 28.6% isobutylene.

In each run, the alkylate product was analyzed and the products were found to have the following compositions and research octane numbers.

| Run | A | B | C | D |
|---|---|---|---|---|
| Alkylate Composition: $C_8-$, wt. % | 7.0 | 7.4 | 7.9 | 6.8 |
| Trimethyl Pentane, wt. % | 77.1 | 76.7 | 76.9 | 73.0 |
| Dimethyl Hexane, wt. % | 11.5 | 11.2 | 11.3 | 13.7 |
| $C_8+$, wt. % | 4.4 | 4.7 | 4.0 | 6.5 |

| Run | A | B | C | D |
|---|---|---|---|---|
| Research Octane Number: | 95.5 | 95.5 | 95.6 | 94.4 |

As can be readily seen, the alkylate product obtained from Runs A, B, and C is superior in quality compared to the prior art process of Run D. This improvement is reflected by increased yield of high octane trimethyl pentane which results in a research octane improvement of greater than one number.

EXAMPLE II

This example contains pilot plant test results for two alkylation process runs, conducted in essentially the same manner as the runs described in Example I. The runs of this example, however, employed a feedstock having a mole ratio of isobutane to $C_4$ olefins of 7.6 and a $C_4$ olefin distribution of 47.9% 2-butene, 23.9% 1-butene, and 28.2% isobutylene. The catalyst used in Run E was identical in composition to that used in Run C of Example I. This run was performed to allow for cross comparison to the catalysts of Example I and to eliminate any affects due to the different feedstock. Run F utilized a catalyst comprised of approximately 12 wt.% tert-amylmethyl ether and 88 wt.% hydrogen fluoride. Both Runs E and F are alkylation processes of the instant invention.

In each run, the alkylate product was analyzed and the products were found to have the following compositions and research octane numbers.

| Run | E | F |
|---|---|---|
| Alkylate Composition: | | |
| $C_8-$, wt. % | 10.6 | 10.6 |
| Trimethyl Pentane, wt % | 71.3 | 72.2 |
| Dimethyl Hexane, wt. % | 11.2 | 11.5 |
| $C_8+$, wt. % | 6.8 | 5.7 |
| Research Octane Number: | 95.1 | 95.0 |

Again, it is readily apparent that the alkylation process of the instant invention yields alkylate rich in trimethyl pentane and having high research octane value.

What is claimed is:

1. A process for the alkylation of an isoparaffin with an olefin-acting agent in the presence of an alkylation catalyst comprising the steps of:
   (a) drying the olefin-acting agent and at least a portion of the isoparaffin in a drying means to produce a dried alkylation feedstock, wherein said drying is performed such that the water content of the alkylation catalyst is maintained at less than 2.0 wt.% based on the total weight of the catalyst;
   (b) contacting the dried alkylation feedstock and recycled paraffin with the alkylation catalyst, which catalyst comprises an anhydrous mixture of from about 0.1 to about 15 wt.% of an ether component selected from the group consisting of tert-butyl ether, methylphenyl ether, tert-amylmethyl ether (TAME), and methyl tert-butyl ether (MTBE) and at least 80 wt.% mineral acid in a reaction zone at alkylation conditions and producing a reaction product effluent containing (i) normally liquid alkylate, (ii) unreacted isoparaffin, (iii) alkylation catalyst, and (iv) polymer products;
   (c) separating the reaction product effluent in a separation zone into (i) a liquid hydrocarbon phase and (ii) a liquid alkylation catalyst phase containing polymer products; and,
   (d) regenerating at least a portion of the liquid alkylation catalyst phase at a rate sufficient to provide a polymer products concentration in the liquid alkylation catalyst phase of less than 15 wt.% based on the total weight of the liquid alkylation catalyst phase.

2. The process of claim 1 further characterized in that the ether component is a mixture of two or more ether species.

3. The process of claim 1 characterized in that the ether component comprises methyl tert-butyl ether.

4. The process of claim 1 further characterized in that the mineral acid is hydrofluoric acid.

5. The process of claim 1 further characterized in that regeneration of the liquid alkylation catalyst is performed in a fractionation column that is used to fractionate the liquid hydrocarbon phase.

6. The process of claim 1 further characterized in that the isoparaffin comprises isobutane and the olefin-acting agent comprises $C_3-C_5$ olefins.

7. The process of claim 1 further characterized in that unreacted isoparaffins are recycled to the reaction zone.

* * * * *